United States Patent
Wehrli

(10) Patent No.: US 9,085,782 B2
(45) Date of Patent: Jul. 21, 2015

(54) ENZYMATIC CLEAVAGE OF STEVIOSIDE TO PRODUCE STEVIOL

(75) Inventor: Christof Wehrli, Witterswil (CH)

(73) Assignee: DSM IP ASSETS B.V., Heerlen (NL)

( * ) Notice: Subject to any disclaimer, the term of this patent is extended or adjusted under 35 U.S.C. 154(b) by 234 days.

(21) Appl. No.: 13/521,796

(22) PCT Filed: Jan. 6, 2011

(86) PCT No.: PCT/EP2011/050124
§ 371 (c)(1),
(2), (4) Date: Jul. 12, 2012

(87) PCT Pub. No.: WO2011/089031
PCT Pub. Date: Jul. 28, 2011

(65) Prior Publication Data
US 2013/0071887 A1    Mar. 21, 2013

(30) Foreign Application Priority Data

Jan. 19, 2010 (EP) .................................... 10151056

(51) Int. Cl.
| | |
|---|---|
| *C12P 15/00* | (2006.01) |
| *C12N 9/26* | (2006.01) |
| *C12N 9/00* | (2006.01) |
| *C12N 1/20* | (2006.01) |
| *C12P 7/42* | (2006.01) |

(52) U.S. Cl.
CPC .. *C12P 7/42* (2013.01); *C12P 15/00* (2013.01)

(58) Field of Classification Search
None
See application file for complete search history.

(56) References Cited

PUBLICATIONS

Grace et al. J Chromatogr B Analyt Technol Biomed Life Sci. Feb. 17, 2006;832(1):158-61. Epub Jan. 18, 2006.*
Melis et al. Braz J Biol. May 2009;69(2):371-4.*
Chica et al. Curr Opin Biotechnol. Aug. 2005;16(4):378-84.*
Sen et al. Appl Biochem Biotechnol. Dec. 2007;143(3):212-23.*
International Search Report for PCT/EP2011/050124, mailed Mar. 3, 2011.
Pezzuto et al., "Metabolically activated steviol, the aglycone of stevioside, is mutagenic", *Proceedings of the National Academy of Sciences*, vol. 82, No. 8, Apr. 1985, pp. 2478-2482.
Gianfagna et al., "Synthesis of [2H]gibberellins from steviol using the fungus *Gibberella fujikuroi*", *Phytochemistry*, vol. 22, No. 2, 1983, pp. 427-430.
Ruddat et al., "Biosynthesis of Steviol", *Archives of Biochemistry and Biophysics*, 1965, pp. 496-499.
Mosettig et al., "Stevioside. II. The Structure of the Aglucon", *Journal of Organic Chemistry*, vol. 20, No. 7, 1955, pp. 884-899.
Hanson et al, "Studies in Terpenoid Biosynthesis II" Phytochemistry, Apr. 1968, vol. 7, No. 4, pp. 595-597.
Kashyap et al, "Applications of pectinases in the commercial sector: a review", Bioresource Technology, May 2001, vol. 77, No. 3, pp. 215-227.
Office Action dated Feb. 27, 2015, issued in connection with Japanese Patent Application No. 2012-548389 (with English translation).

* cited by examiner

*Primary Examiner* — Christian Fronda
(74) *Attorney, Agent, or Firm* — Nixon & Vanderhye P.C.

(57) ABSTRACT

This invention is directed to a process for cleaving glycoside residues from stevioside to produce steviol using a commercially available enzyme mixture containing pectinase, CYTOLASE PCL5®. In preferred methods, the reaction takes place in the presence of a yeast culture. Also described are combinations of *Helix pomatia* enzymes and CYTOLASE PCL5®.

7 Claims, 2 Drawing Sheets

Hydrolysis of rebaudioside A and stevioside

ENZYMATIC CLEAVAGE OF STEVIOSIDE TO PRODUCE STEVIOL

Figure 1:
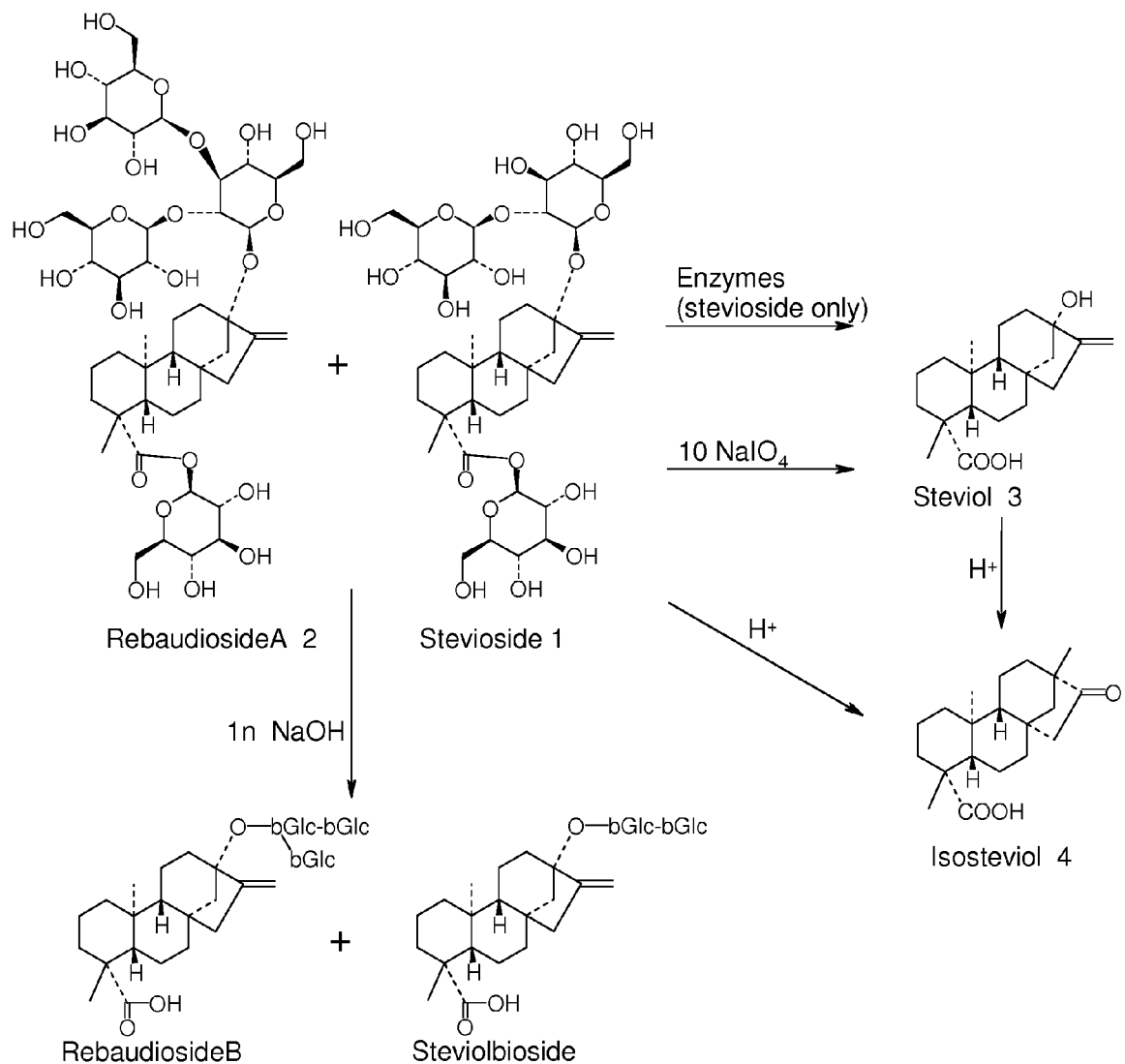

This application is the U.S. national phase of International Application No. PCT/EP2011/050124 filed 6 Jan. 2011 which designated the U.S. and claims priority to EP Patent Application No. 10151056.8 filed 19 Jan. 2010, the entire contents of each of which are hereby incorporated by reference.

BRIEF DESCRIPTION OF THE INVENTION

This invention is directed to a process for cleaving glycoside residues from stevioside to produce steviol using a commercially available enzyme mixture containing pectinase, CYTOLASE PCL5®. In some preferred methods, the reaction takes place in the presence of yeast.

BACKGROUND OF THE INVENTION

*Stevia rebaudiana* contains sweet tasting compounds, namely stevioside and rebaudioside A that are mainly used as calorie-free sweeteners. Steviol is the aglycone derivative of these compounds. Steviol can be used to improve cognitive functions; see e.g. WO 2009/071277 (DSM IP ASSETS, B.V.)

Production of steviol from steviosides is difficult. Acid hydrolysis of stevioside its troublesome because under acidic conditions, the steviol that is produced rearranges into isosteviol. There have even been some literature reports that steviol cannot be obtained through this method (Kohda et al 1976 *Phytochemistry* 15: 981-983.)

An alternative method for cleavage of steviosides to produce steviol using sodium periodate was described by Ogawa et al 1980; *Tetrahedron* 36: 2641-2648. However, this process calls for a highly diluted system and a large excess (about >10 mol equivalents) of the expensive sodium periodate to achieve useful yields. Thus, this process is not economic for producing large amounts of steviol.

There have been a few enzyme-based methods described: Bridel et al 1931 *Bull. Soc. Chimie Biol.* 13:781-96 noted that stevioside was not hydrolyzed by a variety of "fermenting products" such as emulsin, rhamnodiastase, *Aspergillus niger* or macerated and air-dried bottom fermentation yeast. The authors were successful using diastase from the snail (*Helix pomatia*). However, they obtained "barely 0.5 cm$^3$ of pure digestive juice" per animal, and thus is not appropriate for large scale production. Mosettig et al, 1955 *J. Org. Chem.* 20: 884-899 also used enzymatic hydrolysis of the glucosides using snail enzyme preparations refer to as "enzyme juice" and a "dry preparation" to produce small amounts (less than 0.5 grams) of steviol. No further characterization of the enzymes were given.

Khoda et al., supra reported that other authors used a crude hesperidinase to generate steviol from stevioside, but when this was repeated, rebaudioside B and glucose were obtained rather than the desired steviol.

Ruddat et al 1965 *Arch. Biochem. Biophys.* 110: 496-499; Gianfagna et al. 1983 *Phytochemistry* 22(2): 427-430; and Pezzuto et al. 1985 *Proc. Natl. Acad. Sci. USA* 82: 2475-2482 each described a procedure using various commercial pectinases ("Pectinol 59L" from Rohm & Haas; "Pectinol 50L" from Corning Biosystems; "Pectinol AC" from Rohm & Haas, respectively). Davis et al, 1992 *Phytopathology* 82: 1244-50 reported that "Pectinol 59L" was no longer commercially available, and it is not clear if the other pectinols are still sold.

There is a need for an efficient process of producing steviol from steviosides which is suitable for commercial, large scale production.

DETAILED DESCRIPTION OF THE INVENTION

It has been found, in accordance with this invention, that a commercially available enzyme preparation, CYTOLASE PCL5®, is able to cleave stevioside to produce steviol, and can be used in an efficient and commercially feasible process. Thus, one aspect of this invention is a method of producing steviol comprising:
  a) contacting stevioside with a CYTOLASE PCL5® enzyme preparation, and
  b) recovering steviol.

It has also been found, that the sugars (glucose) released during the cleavage can inhibit the above enzymatic reaction. Thus, it is preferred that the above reaction take place in the presence of yeast. The yeast can remove the resultant glucose, and therefore the enzymatic reaction can proceed unhindered. Thus, another aspect of this invention is a method of producing steviol comprising:
  a) contacting stevioside with a CYTOLASE PCL5® enzyme preparation, in the presence of a live yeast culture, and
  b) recovering steviol.

DETAILED DESCRIPTION OF THE FIGURES

Throughout this specification, numbers appearing after compound names refer to the compounds as illustrated in the following figures.

FIG. 1 shows the hydrolysis of rebaudioside A and stevioside

Figure 2:
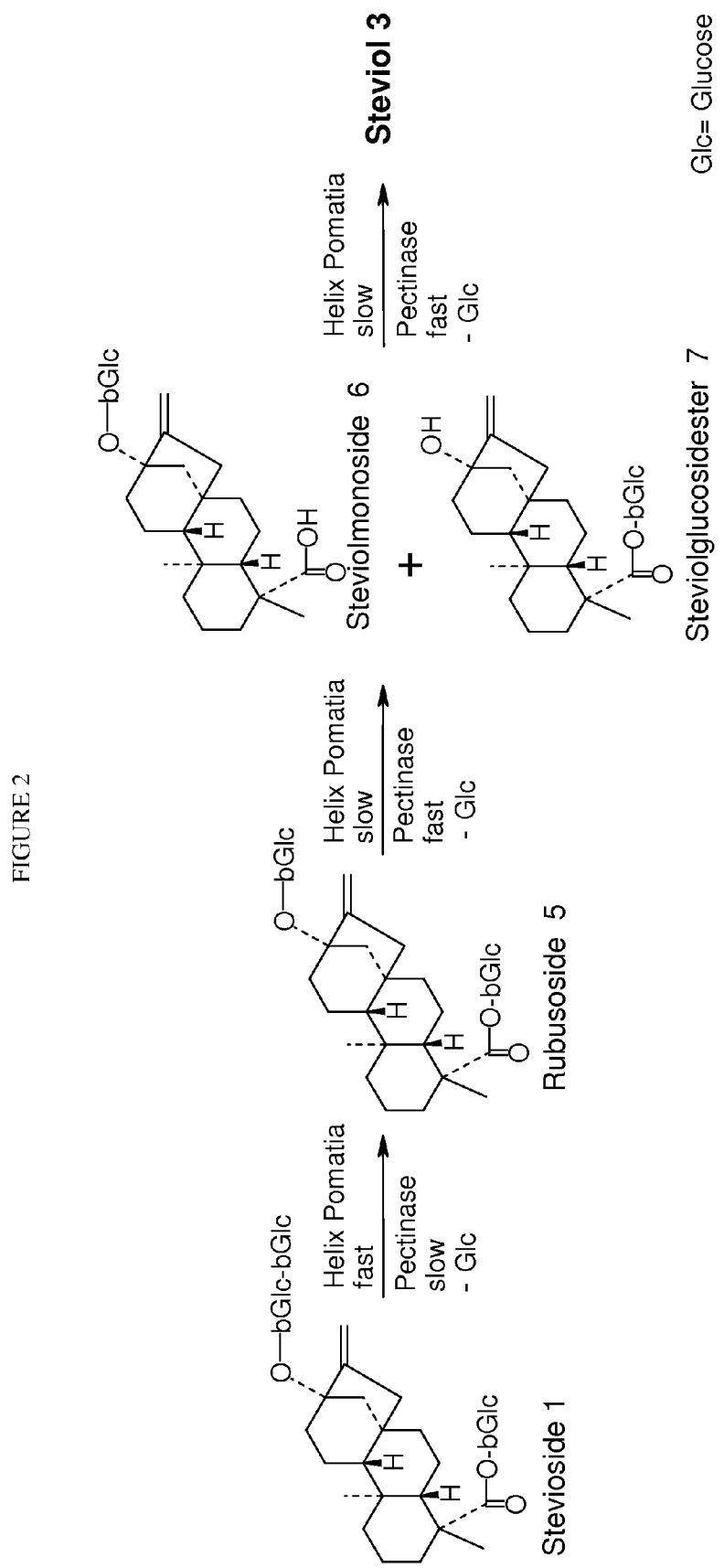

FIG. 2 shows hydrolysis of stevioside by *Helix pomatia* enzymes and pectinases "CYTOLASE PCL5" is an enzymatic preparation commercially available from DSM Food Specialties, Delft, The Netherlands. It is a mixture of enzymes obtained from a selected GRAS strain of *Aspergillus niger*, and includes pectinases and hemicellulases. It is generally used to produce juices having a low content of galacturonic acid and to clarify fruit juice preparations, but there are reports other uses as well:
  its β-D-Glucosidases activities can be used in the manufacture of wine and champagne (see WO1998/38316)
  its β-glucopyranosidase and α-rhamnosidase activities can be used to hydrolyze steroid glycosides to produce desglucodesrhamnoruscin (U.S. Pat. No. 6,911,325).

"Yeast" refers to *Saccharomyces cerevisceae, Saccharomyces pastorianus*, or other yeast species which can be used in large scale fermentations using known techniques, with the proviso that the yeast is able to convert glucose to carbon dioxide and ethanol.

The stevioside starting material for this reaction do not need to be present in a purified or isolated form. In preferred embodiments, they are present in a plant extract which contains steviosides, such as a *Stevia* sp. extract, and more preferably in a *Stevia rebaudiana* extract. Non-cleavable stevioside components may also be present in the extracts. Preferred *Stevia* extracts contain a higher concentration of stevioside, and a lower concentration of non-cleavable steviosides such as rebaudioside A which accumulate over the time course of the reaction and make the process less efficient. The preferred concentrations for stevioside in the extract are at least 50% of total steviosides, preferably >90% by weight. (Stevioside of high content can be readily purchased.

It is unclear exactly which enzymes are appropriate for mediating the reaction which cleaves the sugar from stevioside to produce steviol. For example, some pectinases are suitable, but not others; and similarly, some β-glucuronidases are suitable, but not others. Thus, a number of enzymes and enzyme mixtures were investigated to determine suitability. Of the numerous ones tested, a number of them resulted in no reaction, even after 4 days incubation. At least partial successes were obtained with the following enzymes:

β-Glucanase from *Helix pomatia* (FLUKA 49103);
β-Glucuronidase Type H-3 from *Helix pomatia* (SIGMA G8885);
β-Glucuronidase Type H-2 from *Helix pomatia* (SIGMA G0876);
β-Glucuronidase Type HP-2 from *Helix pomatia* (SIGMA 7017);
Pectinase from *Aspergillus niger* (SIGMA PS4716);
Pectinase from *Aspergillus aculeatus* (SIGMA P2611);
Sulfatase from *Helix pomatia* Type H-1 (SIGMA S9626);
CYTOLASE PCL5® (DSM)

Of the many enzymes, it was found that CYTOLASE PCL5® had good activity and is commercially available, and thus it is the preferred enzyme of this invention.

Further, it was noted that the enzyme is subject to a feedback inhibition by production of the cleaved glucose, but not by steviol (which is not water soluble). Thus, while steviol production at a small scale is possible by incubating CYTOLASE PCL5® with stevioside, in the absence of other reactants, it may not be the most preferred method for large scale production due to glucose accumulation.

However, it has been found, in accordance with this invention, that by fermentation with yeast at 40° C. maximum until the glucose was converted to carbon dioxide and ethanol, restored the enzymatic activity to almost the initial activity. This process can be scaled up to an industrial level suitable for the large scale production of steviol, which has, until now not been possible. Thus, another aspect of this invention is a process for the commercial scale production of steviol comprising contacting stevioside or rebaudioside with CYTOLASE PCL5® in the presence of a yeast culture, under yeast fermentation conditions, and recovering the produced steviol.

If desired, after the fermentation step, an optional further enzymatic hydrolysis of the remaining stevioside, such as that present in a *Stevia* extract, can be used to increase the amount of steviol. As the enzyme preparation is stable at higher temperatures than is the yeast culture, this enzymic hydrolysis step can be performed at a higher temperature than that used to cultivate the yeast. For example, the temperature can be above 40° C., preferably from about 40-60° C., and more preferably at about 55° C. The potential inhibition of the enzymes by the substrate can be avoided by sequential addition of the *Stevia* extract, thus holding the concentration of steviosides at a lower level. Thus, another aspect of this invention is:

a process for the commercial scale production of steviol comprising:
a) providing a yeast culture under fermentation conditions, with stevioside and CYTOLASE PCL5® to produce a culture medium comprising steviol; and
b) hydrolyzing at least a portion of remaining stevioside in the culture medium under increased temperature conditions, to produce a culture medium enriched in steviol.

The culture medium which is enriched in steviol can be used as is, or optionally, the steviol can be separated out, and purified if desired.

The simultaneous hydrolysis of *Stevia* extracts and the fermentation of glucose is possible, but due to $t_{max}$=40° C. of the yeast, the overall hydrolysis rate at 40° C. is lower than the sequential hydrolysis and fermentation.

Combination of Enzymes

It was also found, in accordance with this invention, that a combination of CYTOLASE PCL5® (or Pectinase from *Aspergillus niger* (SIGMA PS4716) or Pectinase from *Aspergillus aculeatus* (SIGMA P2611)) and a second enzyme preparation selected from the group consisting of:

β-Glucuronidase Type H-3 from *Helix pomatia* (SIGMA G8885);
β-Glucuronidase Type H-2 from *Helix pomatia* (SIGMA G0876);
β-Glucuronidase Type HP-2 from *Helix pomatia* (SIGMA 7017);
Sulfatase from *Helix pomatia* Type H-1 (SIGMA S9626);

can hydrolyze the stevioside more efficiently than use of a single enzyme preparation.

As shown in FIG. 2, the enzymes from *Helix pomatia* (vineyard snail) cleaved stevioside (1) rapidly to rubusoside (5), and slowly further to a mixture of steviolmonoside (6) and steviolglucoside ester (7) followed by slow final cleavage to steviol (3). This pattern was observed regardless of whether the enzymes contained mainly sulfatase or glucuronidase activity.

The active pectinases and cytolase cleaved stevioside (1) slowly to rubusoside (5) followed by more rapid hydrolysis to 6/7 and finally into steviol (3). CYTOLASE PCL5® and the active pectinases cleaved stevioside (1) into steviol with similar activity. CYTOLASE PCL5® was used for further development, as this enzyme is allowed for food production and was readily available from DSM.

A mixture of *Helix pomatia* derived enzyme and of a pectinase or CYTOLASE PCL5® was found to cleave stevioside faster and with less enzyme than either alone. *Helix pomatia* enzymes cleaved the first hydrolysis step faster. The pectinases and CYTOLASE PCL5® acted faster on the later hydrolysis steps. Thus, another aspect of this invention is an Particularly preferred enzyme combinations are
CYTOLASE PCL5® and glucuronidase HP2 from *Helix pomatia* Sigma G7017; and
CYTOLASE PCL5® and glucuronidase Type H2 *Helix pomatia* SIGMA G0876.

The following examples are presented to better illustrate the invention.

EXAMPLES

Example 1

Various enzymes and enzyme preparations (collectively referred to as "enzymes" were evaluated for their ability to cleave stevioside and rebaudioside A to produce steviol. 50 mg *Stevia* extract RV140-54 (19% Rebaudioside A, 19% Stevioside [w %]), was solubilized in 5 ml buffer pH 4.1 (0.1 mol/l H3PO4+NaOH), 50 μl enzyme solution or 10 mg lyophilized powder; 40° C. (rem 1). Results are shown in Table 1, below.

TABLE 1

Evaluation of enzymes

| Enzyme/Source | Formation of Steviol |
|---|---|
| Cellulase Onozuka R-10 Merck 102321 | 4 d no reaction |
| Cellulase *Aspergillus niger* FLUKA 22178 | 4 d no reaction |
| β-Glucanase from *Helix pomatia* FLUKA 49103 | 7 d slight formation |
| β-Glucosidase from almonds FLUKA 49290 | 4 d no reaction |
| β-Glucosidase *Aspergillus niger* FLUKA 49291 | 4 d no reaction |
| α-Glucosidase Type V from rice SIGMA G9259 | 4 d no reaction |
| β-Glucuronidase Type H-3 *Helix pomatia* SIGMA G8885 | 4 d complete formation |
| β-Glucuronidase Type H-2 *Helix pomatia* SIGMA G0876 | 4 d complete formation |
| β-Glucuronidase Type HP-2 *Helix pomatia* Sigma 7017 | 5 d partial formation |
| Hesperidinase *Aspergillus niger* SIGMA H8137 | 4 d no reaction |
| Hesperidinase from *Penicillium* sp. SIGMA H8510 | 4 d no reaction |
| Pectinase *Rhizopus* sp. crude powder SIGMA P2401 | 4 d no reaction |
| Pectinase *Aspergillus niger* FLUKA 17389 | 4 d no reaction |
| Pectinase *Aspergillus niger* SIGMA PS2736 | 4 d no reaction |
| Pectinase *Aspergillus niger* SIGMA PS4716 | 6 d partial formation |
| Pectinase *Aspergillus aculeatus* SIGMA P2611 | 6 d partial formation |
| Sulfatase *Helix pomatia* Type H-1 SIGMA S9626 | 4 d complete formation |
| Sulfatase *Patella vulgata* Type IV SIGMA S8504 | 4 d no reaction |
| *Rapidase ADEX-P DSM enzyme 00075 | 4 d no reaction |
| *Rapidase AR2000 DSM enzyme 00071 | 4 d no reaction |
| *Rapidase Press DSM enzyme 00072 | 4 d no reaction |
| *Rapidase TF; DSM enzyme 00071 | 4 d no reaction |
| *Gluco Amylase GA130L DSM enzyme 50022 | 4 d no reaction |
| *Cytolase PCL5 DSM enzyme 00073 | 7 d partial formation |

[1]d = days

None of the enzymes was able to cleave rebaudiosideA, therefore preferred *Stevia* extracts for use as starting materials should contain a high level of stevioside and a low content of rebaudiosideA.

Example 2

Steviol by Enzymatic Hydrolysis of Stevioside

A solution of 3000 ml water, 108 ml CYTOLASE PCL5® and 12 ml glucuronidase HP2 from *Helix pomatia* Sigma G7017; 16.5 g potassium dihydrogenphosphate (Fluka), 120 g stevioside 95% "DAE Pyung" was adjusted at 55° C. to pH=4.2 by addition of about 1.6 ml ortho phosphoric acid 1 mol/l.

The mixture was stirred for 4 d at 55° C. HPLC indicated nearly complete hydrolysis of stevioside into steviol.

The temperature of the fine slurry of steviol was lowered to 40° C. and 2.0 g dry yeast (dried bakers yeast) was added. The mixture was stirred for 24 h at 40° C. until carbon dioxide evolution nearly ceased. The mixture was heated to 55° C. and the pH was adjusted to pH=4.2 by addition of about 16 ml potassium hydroxide 1 mol/l.

To the mixture was added 120 g stevioside 95% "DAE Pyung". The beige slurry was stirred for 6 d at 55° C. HPLC indicated nearly complete hydrolysis of stevioside (1) and the intermediates (5, 6, 7) into steviol (3).

The white slurry was cooled to ambient and filtered by a Buchner funnel. The wet filtercake was suspended in a 3 l reaction flask in 3000 ml ethylacetate at ambient for 1 h. The emulsion was filtered and washed with 200 ml ethylacetate "Fluka 45760".

The organic phase was stirred 45 minutes at ambient temperature in a 3 l reaction flask with 7.5 g charcoal Norit CA1. The black slurry was filtered. The residue was washed with 100 ml ethylacetate. The clear filtrate was concentrated at the rotavapor in the vacuum until a thick slurry was obtained. The suspension was filtered. The procedure was repeated with the filtrate. The filter cakes where combined and dried 18 h in the vacuum. We obtained: 72.1 g Steviol, white light crystals, content: 98% [a %]

Example 3

Steviol by Enzymatic Hydrolysis of Stevioside

A solution of 500 ml water, 36 ml CYTOLASE PCL5® and 20 g stevioside 95% "DAE Pyung". The mixture was stirred for 4 d at 55° C. HPLC indicated nearly complete hydrolysis of stevioside into steviol. The precipitate of steviol was filtered and washed with water. The residue was dried in the vacuum. We obtained 7.29 g steviol of 91% content.

Example 4

Hydrolysis of Stevioside with "GlucuronidaseH230 Cytolase PCL5" (Enzyme Mixture 1:4)

Conditions:

100 mg Stevioside, content=98%;

20 μl β-Glucuronidase Type H2 *Helix pomatia* SIGMA G0876;

80 μl CYTOLASE PCL5®;

Buffer 0.01 mmol/l phosphate pH=4.2;

48 h; 45° C.

TABLE 2

| | Stevioside 1 | Intermediates 5* + 6* + 7* | Steviol 3 |
|---|---|---|---|
| 1.0% Stevioside | 29% | 15% | 47% |
| 1.0% Stevioside + 1.0% glucose | 60% | 27% | 13% |

*refers to compounds numbered as in FIG. 2.

The enzymes are inhibited by the product glucose. The inhibition of the enzymes by the glucose without removal of the glucose would prolong the reaction time and limit the maximal concentration.

Example 5

Influence of Yeast, Removal of the Glucose

Conditions:
100 mg Stevioside, content=98%;
40 yl β-Glucuronidase Type H-2 *Helix pomatia* SIGMA G0876;
160 yl CYTOLASE PCL5®;
Buffer 0.01 mmol/l phosphate pH=4.2;
24 h at 35° C.; 71 h at 50° C.

The glucose formed by the cleavage of stevioside inhibits further cleavage by the enzymes. Dried bakers yeast successfully removed the glucose without influencing the hydrolysis by the enzymes. The treatment with yeast was done at ≤40° C., as at 45° C. the yeast was inactivated within several hours. The enzymes regained full activity after conversion of the glucose to carbon dioxide and ethanol. At 40° C. the simultaneous cleavage and fermentation of glucose is possible, albeit the overall reaction rate is lower than with the sequential method (6 days hydrolysis at 55° C. and 1 day fermentation at 40° C.). Data is presented in TABLE 3, below.

TABLE 3

| Concentration in buffer | Stevioside1 | Intermediates 5* + 6* + 7* | Steviol 3 |
|---|---|---|---|
| 1.0% Stevioside 1% glucose | 34% | 19% | 44% |
| 1.0% Stevioside 1% glucose 5 mg dried yeast | 5% | 2% | 84% |

*refers to compounds numbered as in FIG. 2.

What is claimed is:

1. A method for producing steviol, comprising:
contacting stevioside with an enzyme preparation of pectinases and hemicellulases from *Aspergillus niger*, and recovering the steviol.

2. A method according to claim 1, wherein the stevioside is present in a plant extract.

3. A method according to claim 1, wherein the plant extract is a *Stevia* sp. extract.

4. A method according to claim 3 wherein the *Stevia* extract contains an extract containing at least 50% steviosides.

5. A method according to claim 1, wherein the step of contacting stevioside with the enzyme preparation occurs in the presence of a live yeast culture in a culture medium, under conditions wherein steviol is produced in a culture medium.

6. A method according to any of claim 5 further comprising hydrolyzing at least a portion of remaining stevioside in the culture medium at a temperature between 40 and 60° C., to produce a culture medium enriched in steviol.

7. A method according to claim 1 wherein the enzyme preparation also comprises a pectinase from *Aspergillus* sp.

* * * * *